United States Patent
Baust et al.

(10) Patent No.: US 10,182,859 B2
(45) Date of Patent: Jan. 22, 2019

(54) MEDICAL DEVICE FOR THE TRANSPORT OF SUBCOOLED CRYOGENIC FLUID THROUGH A LINEAR HEAT EXCHANGER

(75) Inventors: John M. Baust, Owego, NY (US);
John G. Baust, Owego, NY (US); Roy Cheeks, Harper's Ferry, WV (US);
Anthony Robilotto, Binghamton, NY (US); Kristi Snyder, Candor, NY (US)

(73) Assignee: Endocare, Inc., Austin, TX (US)

( * ) Notice: Subject to any disclaimer, the term of this patent is extended or adjusted under 35 U.S.C. 154(b) by 744 days.

(21) Appl. No.: 12/548,321

(22) Filed: Aug. 26, 2009

(65) Prior Publication Data

US 2010/0057064 A1    Mar. 4, 2010

Related U.S. Application Data

(60) Provisional application No. 61/093,904, filed on Sep. 3, 2008.

(51) Int. Cl.
  *A61B 18/02*    (2006.01)

(52) U.S. Cl.
  CPC ...... *A61B 18/02* (2013.01); *A61B 2018/0212* (2013.01); *A61B 2018/0262* (2013.01); *A61B 2018/0281* (2013.01); *A61B 2018/0287* (2013.01)

(58) Field of Classification Search
  CPC ................ A61B 2018/1445; A61B 2018/1447
  USPC ............................... 606/20–26; 165/156, 184
  See application file for complete search history.

(56) References Cited

U.S. PATENT DOCUMENTS

| | | | |
|---|---|---|---|
| 3,794,039 A | | 2/1974 | Kollner et al. |
| 4,082,096 A | | 4/1978 | Benson |
| 4,367,791 A | * | 1/1983 | Asami ................ F16L 9/19 165/109.1 |
| 4,377,168 A | | 3/1983 | Rzasa et al. |
| 4,418,544 A | * | 12/1983 | Heybutzki et al. .......... 62/50.6 |
| 4,829,785 A | * | 5/1989 | Hersey .................. 62/467 |
| 5,147,355 A | | 9/1992 | Friedman et al. |
| 5,237,824 A | | 8/1993 | Pawliszyn |
| 5,334,181 A | * | 8/1994 | Rubinsky ............ A61B 18/02 606/20 |
| 5,423,807 A | | 6/1995 | Milder |
| 5,452,582 A | | 9/1995 | Longsworth |

(Continued)

FOREIGN PATENT DOCUMENTS

WO    2010028409    3/2010

OTHER PUBLICATIONS

Bartlett, Dean A. "The Fundamentals of Heat Exchangers", Industrial Physics, (1996), pp. 18-21.*

(Continued)

*Primary Examiner* — Ronald Hupczey, Jr.

(57) ABSTRACT

A cryogenic medical device for delivery of subcooled liquid cryogen to various configurations of cryoprobes is designed for the treatment of damaged, diseased, cancerous or other unwanted tissues. The device is a closed or semi-closed system in which the liquid cryogen is contained in both the supply and return stages. The device comprises a number of parts including a vacuum insulated outer dewar, submersible cryogen pump, baffled linear heat exchanger, return chamber, and a series of valves to control the flow of the liquid cryogen. The cryogenic medical device promotes the sub-cooling to any external cryogenic probe.

23 Claims, 3 Drawing Sheets

(56) References Cited

U.S. PATENT DOCUMENTS

| | | | |
|---|---|---|---|
| 5,654,218 A | 10/1997 | Rubinsky et al. | |
| 5,733,280 A | 3/1998 | Avitall | |
| 5,746,736 A | 5/1998 | Tankovich | |
| 5,758,505 A * | 6/1998 | Dobak et al. | 62/6 |
| 5,759,182 A * | 6/1998 | Varney et al. | 606/21 |
| 5,916,212 A | 6/1999 | Baust et al. | |
| 5,951,546 A | 12/1999 | Lorentzen | |
| 6,096,032 A * | 8/2000 | Rowland | 606/20 |
| 6,161,543 A | 12/2000 | Cox et al. | |
| 6,171,301 B1 | 1/2001 | Nelson et al. | |
| 6,306,129 B1 * | 10/2001 | Little et al. | 606/23 |
| 6,468,268 B1 | 10/2002 | Abboud et al. | |
| 6,468,269 B1 | 10/2002 | Korpan et al. | |
| 6,497,703 B1 * | 12/2002 | Korteling et al. | 606/23 |
| 6,887,234 B2 | 5/2005 | Abboud et al. | |
| 7,160,291 B2 | 1/2007 | Damasco et al. | |
| 7,207,985 B2 | 4/2007 | Duong et al. | |
| 7,303,554 B2 | 12/2007 | Lalonde et al. | |
| 7,306,589 B2 | 12/2007 | Swanson | |
| 7,416,548 B2 | 8/2008 | Baust et al. | |
| 7,416,551 B2 | 8/2008 | Ad | |
| 2001/0021847 A1 | 9/2001 | Abboud et al. | |
| 2003/0055416 A1 | 3/2003 | Damasco et al. | |
| 2004/0215295 A1 * | 10/2004 | Littrup et al. | 607/96 |
| 2005/0090814 A1 * | 4/2005 | Lalonde et al. | 606/22 |
| 2005/0261671 A1 * | 11/2005 | Baust et al. | 606/22 |
| 2005/0261753 A1 * | 11/2005 | Littrup et al. | 607/96 |
| 2006/0079867 A1 | 4/2006 | Berzak et al. | |
| 2006/0129142 A1 | 6/2006 | Reynolds | |
| 2006/0235375 A1 | 10/2006 | Littrup et al. | |
| 2007/0021741 A1 | 1/2007 | Abboud et al. | |
| 2007/0151713 A1 * | 7/2007 | Lee et al. | 165/109.1 |
| 2007/0233055 A1 | 10/2007 | Abboud et al. | |
| 2007/0244474 A1 | 10/2007 | DeLonzor et al. | |
| 2007/0277550 A1 | 12/2007 | Li et al. | |
| 2008/0009845 A1 | 1/2008 | Duong et al. | |
| 2008/0027422 A1 * | 1/2008 | Vancelette et al. | 606/23 |
| 2008/0147056 A1 | 6/2008 | van der Weide et al. | |
| 2008/0173028 A1 | 7/2008 | Littrup et al. | |
| 2008/0255551 A1 | 10/2008 | DeLonzor | |
| 2008/0300584 A1 | 12/2008 | Lentz et al. | |
| 2009/0012510 A1 | 1/2009 | Bertolero et al. | |
| 2009/0281533 A1 | 11/2009 | Ingle et al. | |
| 2009/0318913 A1 | 12/2009 | Li | |
| 2010/0057064 A1 | 3/2010 | Baust et al. | |
| 2010/0057067 A1 | 3/2010 | Baust et al. | |
| 2010/0241112 A1 | 9/2010 | Watson | |
| 2011/0152849 A1 | 6/2011 | Baust et al. | |

OTHER PUBLICATIONS

Fladerer et al. "Homogenous nucleation and droplet growth in supersaturated argon vapor: The cryogenic nucleation pulse chamber," Journal of Chemical Physics (2006), vol. 124. 2006 American Institute of Physics. USA.

Office Action dated Aug. 14, 2012 received in related U.S. Appl. No. 12/553,005.

Final Office Action dated Jan. 18, 2013 received in related U.S. Appl. No. 12/553,005.

* cited by examiner

MEDICAL DEVICE FOR THE TRANSPORT OF SUBCOOLED CRYOGENIC FLUID THROUGH A LINEAR HEAT EXCHANGER

RELATED APPLICATIONS

The present application claims priority to U.S. Provisional Patent Application Ser. No. 61/093,904 filed on Sep. 3, 2008 and titled Medical Device for the Transport of Subcooled Cryogenic Fluid through a Linear Heat Exchanger, which is incorporated herein by reference in its entirety.

FIELD OF THE INVENTION

The present invention relates generally to the medical technology field and, in particular, to a medical device for use in a cryogenic system.

BACKGROUND OF THE INVENTION

Over a recent number of years, there has been a strong movement within the surgical community toward minimally invasive therapies. The main goals of the minimally invasive therapies include: 1) eradication of targeted tissue, 2) decreased hospitalization time, 3) limited postoperative morbidities, 4) shortened return interval to daily functions and work, and 5) reduced overall treatment cost. Cryotherapy is a minimally invasive method of treating a disease state through tissue freezing with thousands of patients now receiving the procedure annually. Currently, cryotherapy is used to treat numerous disease states including organ confined tumors such as prostate, kidney, liver, as well as cardiovascular disease, retinal detachment, pain management, and other illness/disease states.

Cryotherapy is an effective yet minimally invasive alternative to radical surgery and radiation therapy. The procedure is done under either general or epidural anesthesia. Since it is minimally invasive, it offers patients a quicker recovery and reduced severity of potential side effects. Without the expense associated with major surgery or an extended hospital stay, cryotherapy is a cost-effective treatment option.

The approaches utilized to date have focused on the delivery of liquid cryogen through the use of moderate to high pressure on the entire system or piston/bellows compression to drive fluid movement. Further, the use of heat exchangers have been limited to coils placed into a bath of cryogen to allow for time consuming, inefficient passive subcooling of the cryogen in which activation of these devices circulate a cryogen (such as liquid nitrogen) to a probe to create a heat sink, thus resulting in tissue freezing.

There exists a need for improvements in cryotherapy, and medical devices or components associated with the treatment to better circulate liquid cryogen to a cryoprobe and facilitate improved measures for treatment and cost. The medical device of the present invention will allow for the circulation (cooling, delivery, and return) of liquid cryogen to a cryoprobe for the freezing of targeted tissue. The invention will facilitate the eradication of tissue, decrease hospitalization time, limit postoperative morbidities, shorten return to daily functions and work, and further reduce the overall treatment cost. Desirably, these improvements to device design and application will also increase its utilization for the treatment of multiple disease states.

SUMMARY OF THE INVENTION

The following invention is a cryogenic medical device designed to deliver subcooled liquid cryogen to various configurations of cryoprobes for the treatment of damaged, diseased, cancerous or other unwanted tissues. The device is a closed or semi-closed system in which the liquid cryogen is contained in both the supply and return stages. The device is vented to the surrounding atmosphere through an adjustable pressure vent to prevent excess pressure buildup while in operation. The device comprises a number of parts including a vacuum insulated outer dewar, submersible cryogen pump, baffled linear heat exchanger, return chamber, and a series of valves to control the flow of the liquid cryogen. In general terms, the outer dewar comprises a submersible rotary pump to drive liquid cryogen through the baffled linear heat exchanger. The linear heat exchanger comprises a tube-within-a-tube whereby a vacuum is applied to the outer chamber to subcool an isolated reservoir of liquid cryogen. The inner chamber comprises a series of baffles and a central spiral to increase the flow path of the liquid cryogen while providing for increased contact based surface area with the outer chamber to allow for more effective heat transfer and subcooling of the cryogen being delivered to the probe. Following circulation to the cryoprobe, cryogen (liquid and gas) is returned to the device into a return chamber which surrounds the supply chamber thereby providing for a staged secondary subcooling chamber for the cryogen in the supply tube. The return chamber is open to the main dewar tank thereby allowing for exchange of liquid and gas between the supply and return chambers. Device operation is controlled and monitored by a series of pressure and vacuum valves designed to control the flow, cooling, pressurization, etc. of the liquid cryogen. This control is achieved through various configurations of manual and computer controlled systems.

One embodiment of the cryogenic system described herein comprises a container filled with liquid cryogen, at least one cryoprobe outside said container for use in cryotherapeutic procedures, a heat exchanger surrounded by said container or a subcooling chamber, a pump which delivers the liquid cryogen to said heat exchanger to subcool the cryogen, an exit port where one or more of said cryoprobes are attached, at least one supply line connected to said heat exchanger and to said exit port, said supply line directing the liquid cryogen to said cryoprobe, and at least one return line which returns liquid cryogen to the container, wherein said container integrates said supply line and said return line with said heat exchanger to form a closed system, said return line configured to redirect the liquid cryogen back into said container. In one embodiment, the cryogenic system is an electronically controlled system and monitored by computer systems.

In one embodiment, the heat exchanger is baffled and provides an interior central component within the interior lumen of the inner chamber that circulates the flow of the liquid cryogen. The cryogenic system further comprises a return chamber surrounding the supply line between an exit opening of the heat exchanger and the exit port such that the return chamber receives the liquid cryogen returned from the cryoprobe by way of the return line. In one aspect, the return chamber includes a secondary heat exchanger so that the return line passes through the secondary heat exchanger to subcool the liquid cryogen in the return line. In another aspect, the cryogenic system uses the container to receive the liquid cryogen returned from the cryoprobe, the container of which insulates the supply line and the return line.

One method of delivering liquid cryogen to a cryoprobe, comprises the steps of (a) providing a device for containing liquid cryogen, said device having one or more openings to allow excess gas or liquid overflow to exit and at least one exit port where one or more cryoprobes is attached; a submersible pump positioned within said device; a heat exchanger positioned within said device; one or more supply lines connecting said submersible pump to said heat exchanger and exiting said heat exchanger to said exit port; a return chamber surrounding said one or more supply lines; and one or more return lines exiting said return chamber and connected to said one or more cryoprobes through said exit port; wherein said one or more supply lines and said one or more return lines form a closed system; (b) filling said device with the liquid cryogen; (c) pumping the liquid cryogen through said submersible pump and into said heat exchanger; (d) subcooling the liquid cryogen within said linear heat exchanger; (e) delivering the liquid cryogen through said one or more supply lines to said exit port which attaches to said one or more cryoprobes; (f) returning the liquid cryogen through said one or more return lines into a return chamber of said device; and (g) recirculating the liquid cryogen through said device for reuse in delivering liquid cryogen to said one or more cryoprobes.

In one embodiment, the method includes a step of subcooling the liquid cryogen within the heat exchanger in which the flow path of the liquid cryogen increases within said heat exchanger. In one aspect, an internal component within the heat exchanger circulates the liquid cryogen. In another aspect, a series of baffles within the heat exchanger emanate into the flow path of the liquid cryogen and provide an enhanced surface area for reducing the temperature of the liquid cryogen within said heat exchanger.

Although pressurization of the liquid cryogen may not be included within the method described above, an additional step of pressurizing the liquid cryogen within the closed system may be advantageous. In one aspect, one or more control valves positioned therein are capable of being electronically manipulated. The control valves may have control over supply of the liquid cryogen, temperature, pressure, and other metrics to allow the safe operation of the cryogenic system.

One embodiment of a device for use in a cryogenic system comprises: one or more walls providing an internal lumen for containing liquid cryogen, said walls having one or more openings which allow for venting of excess gas or liquid overflow, and at least one opening providing an exit port where one or more external cryoprobes are attached; a submersible pump positioned within said internal lumen; a heat exchanger positioned within said internal lumen and capable of integrating a subcooling chamber; one or more supply lines connecting said submersible pump to said heat exchanger and exiting said heat exchanger to said exit port; a return chamber surrounding said one or more supply lines; and one or more return lines exiting said return chamber and connected to said one or more external cryoprobes through said exit port; wherein said one or more supply lines and said one or more return lines form a closed system that provides for supply and return of the liquid cryogen to said heat exchanger within said internal lumen, said heat exchanger providing an enhanced surface area for reducing temperature of the liquid cryogen. In one aspect, the device comprises an inner tubular unit or internal structure which circulates the flow of liquid cryogen through the interior lumen of the chamber. In another aspect, the heat exchanger of the device comprises a series of baffles emanating into the flow path of the liquid cryogen, said series of baffles increasing the surface area within the heat exchanger and thereby further reducing the temperature of the liquid cryogen.

BRIEF DESCRIPTION OF THE DRAWINGS

The invention is best understood from the following detailed description when read with the accompanying drawing figures. It is emphasized that the various features are not necessarily drawn to scale. In fact, the dimensions may be arbitrarily increased or decreased for clarity of discussion.

DETAILED DESCRIPTION

In the following detailed description, for purposes of explanation and not limitation, exemplary embodiments disclosing specific details are set forth in order to provide a thorough understanding of the present invention. However, it will be apparent to one having ordinary skill in the art that the present invention may be practiced in other embodiments that depart from the specific details disclosed herein. In other instances, detailed descriptions of well-known devices and methods may be omitted so as not to obscure the description of the present invention.

Figure 1:
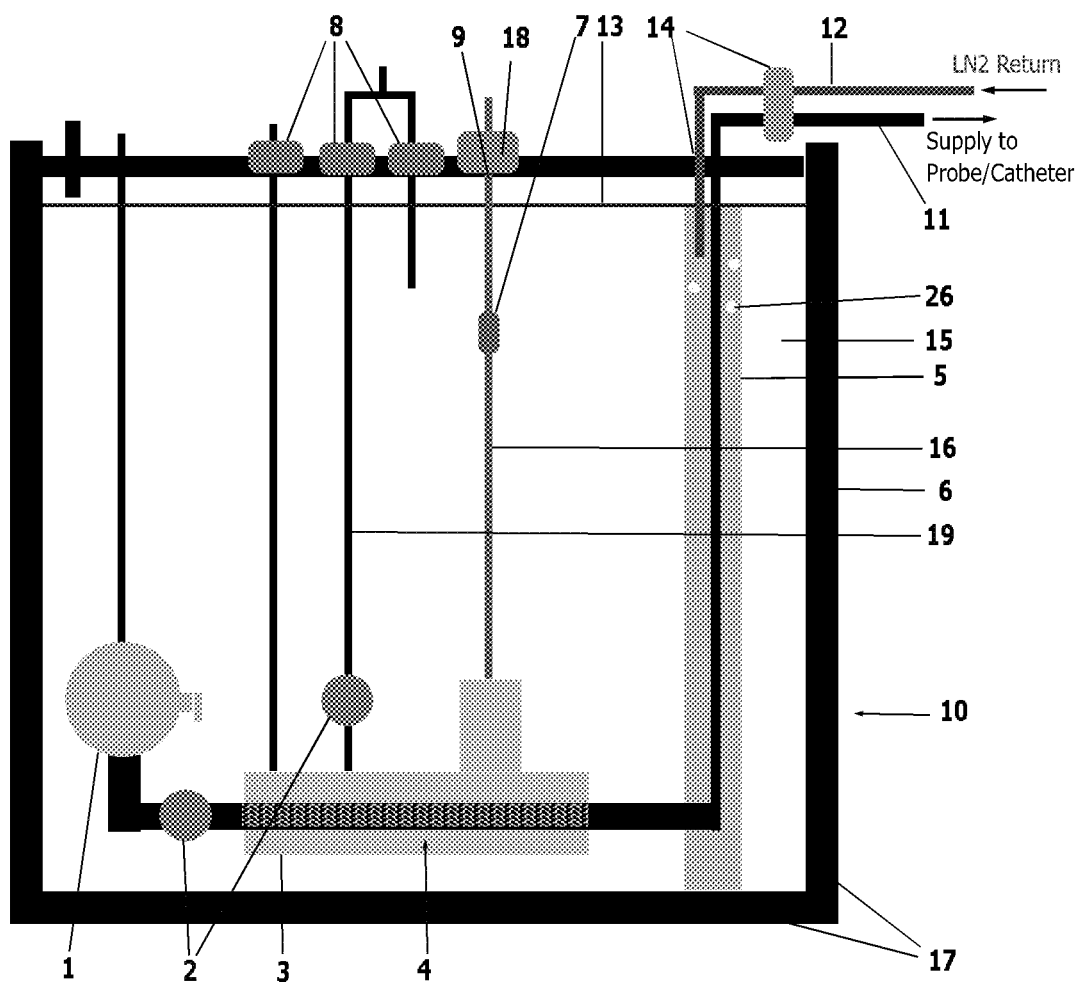
FIG. 1 is a side view of an illustrative embodiment of the device of the present invention.

An external view of a device and system 10 in accordance with one embodiment of the present invention is shown in FIG. 1. The cryogenic system or device 10 has side walls 17 enclosing an internal area, or lumen 15. The device 10 in this embodiment takes the form of a vacuum insulated dewar 6 which stores liquid cryogen in connection with a supply line 11 and return line 12 to a probe or catheter (not shown) to form a closed system 10. The dewar 6 may be made of material such as stainless steel or any other material known for providing a vacuum insulated vessel. The dewar 6 is filled with liquid nitrogen or other liquefied gas (here, discussing as cryogen) to a maximum level 13. Internal to the dewar is a submersible pump 1 which delivers the liquid cryogen to a linear heat exchanger 4 to subcool the cryogen. A subcooling vacuum chamber 3 may surround a heat exchanger 4 facilitating the delivery of subcooled cryogen to an attached cryprobe (also referred to as probe or catheter). The subcooling chamber 3 in connection with the heat exchanger 4 at an entrance and an exit opening form an integral unit for supplying subcooled liquid cryogen. From the heat exchanger, then, the subcooled cryogen passes into a supply line 11 and continues out through an exit port 14 where various configurations of cryoprobes are attached.

The cryogen is returned (as demonstrated by the arrows in FIG. 1) from the cryoprobe via a return tube 12 into a return chamber/cylinder 5 of the dewar 6. The return tube 12 connects into the return cylinder 5 which also surrounds the supply tube 11 that exits the heat exchanger 4. One or more exit ports 14 may be included in a side wall 17 of the dewar 6 or may be a separate unit 14 to incorporate various control valves.

In operation, the device 10 is a closed system allowing for the supply, return, collection, and re-utilization of liquid cryogen during its utilization in the medical/surgical field. The device 10 may or may not be pressurized during operation. The device may also be vented to the surrounding environment to prevent excess pressure buildup during operation.

In one aspect, the returning cryogen empties into the return cylinder or chamber 5. In another aspect, the returning cryogen may empty as bulk fluid into the internal lumen 15 within the dewar 6.

In one embodiment of the present invention, the linear heat exchanger 4 subcools the liquid cryogen prior to delivery to tissue. The heat exchanger 4 comprises a chamber within a chamber configuration such that a vacuum chamber 3 is a subcooling chamber 3, a sealed cylinder 3 filled with liquid cryogen upon which a vacuum is drawn to reduce the atmospheric pressure on the cryogen, in which the temperature of the cryogen within the subcooling chamber 3 is reduced even further. The subcooling chamber 3 further comprises valve controlled ports 8 external to the maximum liquid cryogen level. In one aspect, a vacuum 18 can be drawn on connecting line 16 at a controlled internal valve 7 or external valve 9. The vacuum 18 can also be utilized for attachment to the cryoprobe. In another aspect, valve controlled ports 8 may be accessible for delivery of liquid cryogen to the subcooling chamber 3 by way of a supply line 19 or as a vent 8 for any excessive gas coming from the subcooling chamber 3.

In this embodiment, the linear heat exchanger 4 is an inner chamber 4 which passes through subcooling chamber 3 and connected via the entrance and exit openings. Liquid cryogen passing through the inner chamber 4 is reduced in temperature to a subcooling degree by the outer subcooling chamber 3.

Figure 2A:
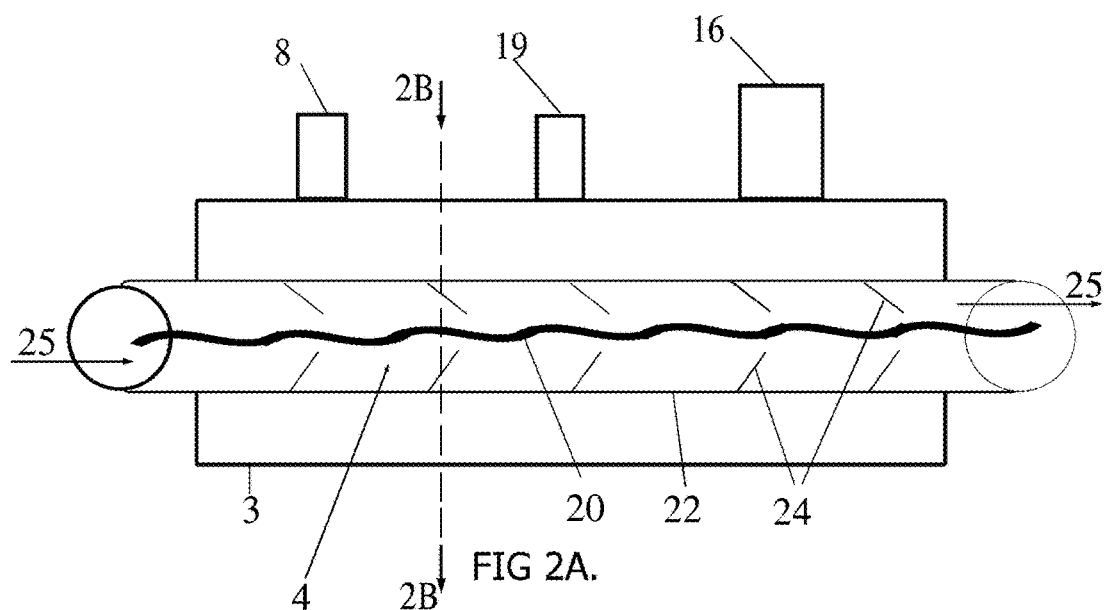
FIG. 2A is a side view of one embodiment of a heat exchanger of the present invention.
Figure 2B:
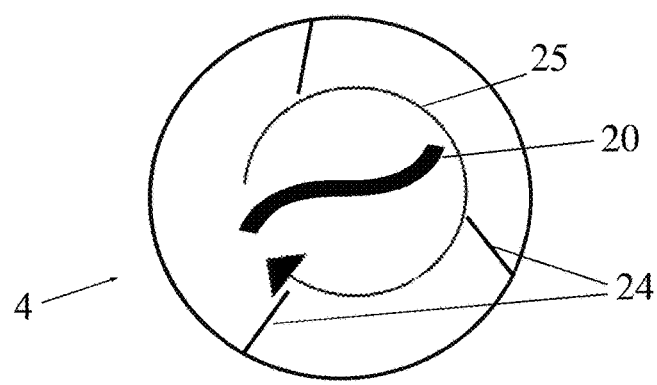
FIG. 2B is a cross-sectional view of FIG. 2A, a front view of one embodiment of a device of the present invention.

Aspects of the linear heat exchanger 4 are illustrated in FIGS. 2A, 2B and FIGS. 3A, 3B. FIG. 2A illustrates a side view of a linear baffled heat exchanger 4. FIG. 2B depicts a cross-sectional of FIG. 2A, a front view of the linear baffled heat exchanger 4 when looking into the inner chamber 4. An interior central component 20, a spiral 20, within the interior lumen of the chamber 4 operates like a corkscrew to increase the flow path 25 of the liquid cryogen. An outer wall 22 of the inner chamber 4 also comprises baffles 24 which increase the surface area in the heat exchanger for quicker and reduced cooling of the liquid cryogen. As illustrated, a series of baffles 24 emanate into the flow path 25 (as illustrated by arrows) of the cryogen in the inner lumen, thereby increasing the surface area in the heat exchanger 4. The spiral component, however, may be any size and shape as to efficiently increase the flow of liquid cryogen. Planar structures, as described below, or any additional features included to increase surface area may further be incorporated.

Figure 3A:
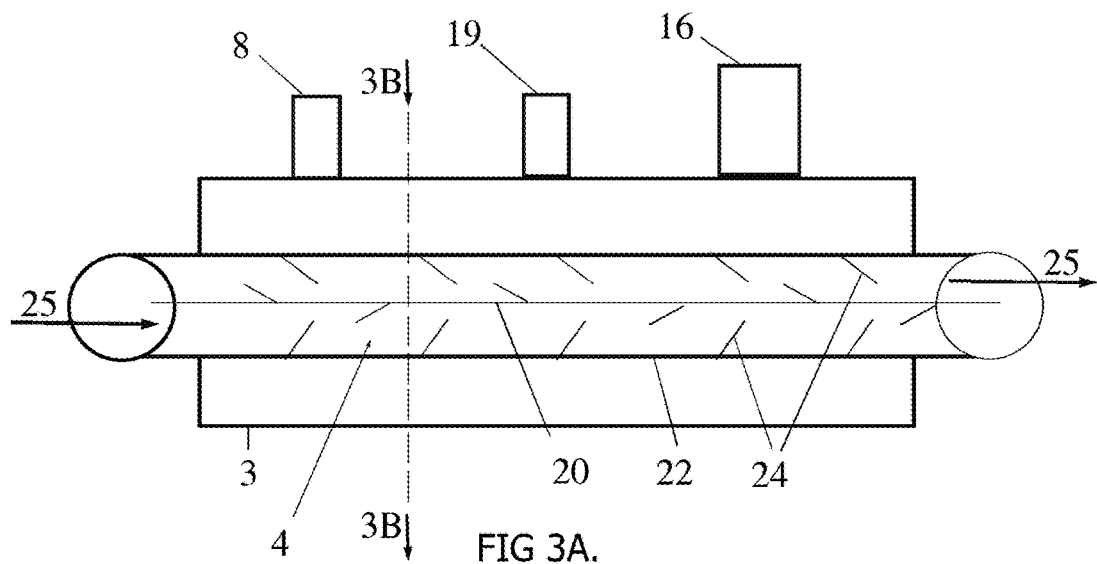
FIG. 3A illustrates a side view of one embodiment of a heat exchanger of the present invention.
Figure 3B:
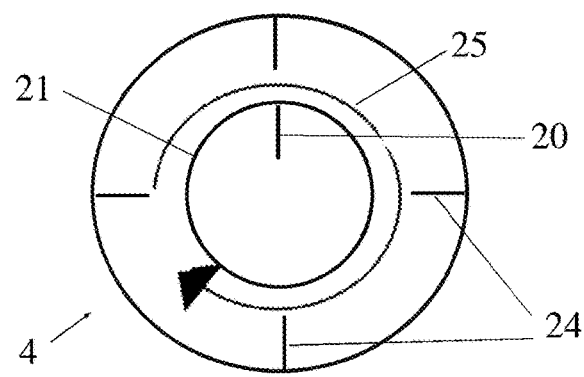
FIG. 3B is a cross-sectional view of FIG. 3A, one aspect of fluid flow through one embodiment of a heat exchanger of the device.

FIG. 3A illustrates another embodiment of a linear heat exchanger 4 such that the internal component or structure 20 has a planar configuration and also operates in a circular motion to increase the flow 25 of the liquid cryogen. FIG. 3B depicts a cross-section of FIG. 3A such that the inner tubular unit 21 assists the internal structure 20 in circulating the flow of liquid cryogen through the interior lumen of the chamber 4.

One embodiment of the medical device comprises a return chamber 5 which is illustrated as a return cylinder 5 in FIG. 1 such that the return chamber 5 surrounds the supply line 11 coming from the heat exchanger 4. The return chamber 5 and the surrounded supply line may then provide a secondary heat exchanger for the system/medical device 10. Cryogen return is vented into the return chamber 5. In one aspect, the return chamber 5 comprises a series of vent holes 26 near the top of the return chamber 5 to allow for the venting of gas and/or liquid overflow into the main dewar 6. Vent holes 26 allow for the reutilization of cryogen and thus extend the operation time for the medical device 10. In another aspect, the return tube 12 is vented into the main dewar 6 either directly or by first passing through a linear heat exchanger (similar to the combination of heat exchanger 4 and subcooling chamber 3) to subcool the return cryogen prior to venting into the main dewar 6. Return of the cryogen to the main dewar 6 allows the cryogen to return through a heat exchanger such that the cryogen is reutilized and extends the operation time even longer.

In another embodiment, the medical device 10 may provide a system which is controlled electronically or through a series of computer controlled valves including any heaters, sensors, motors, or gauges. The sensors monitor pressure, temperature, fluid level in the dewar and can measure any metric as may be desired. In one aspect, the sensors monitor pressure levels within defined safety ranges. In another aspect, the sensors may control the pressurization of one or more components internal to the dewar. Any of the valves 2, 7, 8, 9, including exit portal valve 14, may be automated to enable a controlled and consistent operation of the cryogenic system.

In utilizing the medical device of the present invention, various methods in the industry may be employed in accordance with accepted cryogenic applications. As discussed, the embodiments of the present invention are for exemplary purposes only and not limitation. Advantageously, this device represents an important step in targeted thermal therapies. Various cryosurgical devices and procedures to apply freezing temperatures to a target tissue may be employed for use with the medical device of the present invention. The medical device of the present invention has been developed to enable and improve some of the approaches used to target or ablate tissue. Furthermore, the medical device can couple controlled pumping of a liquid cryogen through a baffled linear heat exchanger to decrease the overall temperature of the cryogen providing a greater heat capacity of the fluid and thereby resulting in an increased cooling potential in a cryoprobe.

Thus, the invention facilitates other improvements in cryotherapy, and medical devices or components associated with the treatment. The medical device of the invention allows for the circulation (cooling, delivery, and return) of liquid cryogen to a cryoprobe for the freezing of targeted tissue. The invention facilitates the eradication of tissue and can thereby decrease hospitalization time; and further limit postoperative morbidities, shorten return to daily functions and work, and further reduce the overall treatment cost. These improvements to device design and application can also increase utilization of the device for the treatment of multiple disease states.

The current device represents an improved development of cryosurgical devices by allowing for controlled linear flow of a cryogen without the need for high pressure or compression based bellows or piston systems. Further, the device contains a novel baffled linear heat exchanger designed for cryogen flow through a specialized subcooling chamber.

The embodiments of the present invention may be modified to take the shape of any device, container, apparatus, or vessel currently used in industry. Specifically, cylindrical or alternative vessels may provide containers for the cryogenic system for improved cryogenic supply and delivery. Further, any compartmental arrangement in combination with the components of the above system may take many forms and be of any size, shape, or passageway. Any number of vents may also be utilized to facilitate operation of the system. The system may also be a partially closed or completely closed system.

In one embodiment of the system, the device is contained within a shell or enclosure that allows the system to be easily transported. The enclosure may then include any mobile feature such as wheels, handles, and fixtures (or allow placement onto a cart having these features) so that the system can be transported to and from the location of treatment. Such mobility allows the system to be easily moved to and from an operating room or site of therapeutic treatment. It is also noted that the system is readily separable from the cryogen fill tanks and fill lines that initially supply the system with the liquid nitrogen or other such cryogenic fluid. This improved feature eliminates the bulkiness of standard cryogenic medical devices.

As presented, the multiple embodiments of the present invention offer several improvements over standard medical devices currently used in cryogenic industry. The improved cryogenic medical devices remarkably enhance its utilization for the cooling, delivery and return of a liquid cryogen to a cryoprobe for the freezing of targeted tissue. The present invention provides cost savings and significantly reduced treatment times which further reduce expenditures in the healthcare setting. The previously unforeseen benefits have been realized and conveniently offer advantages for the treatment of multiple disease states. In addition, the improvements enable construction of the device as designed to enable easy handling, storage, and accessibility. Further uses of the system outside of the healthcare setting are foreseeable. Potential uses in the space industry, defense systems or any industry requiring rapid cooling may incorporate the cryogenic system as thus described.

As exemplified, the device may include any unitary structure, vessel, device or flask with the capacity to integrally incorporate any combination of such structures. The invention being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their legal equivalents.

What is claimed is:

1. A cryogenic system comprising:
   a container comprising one or more walls providing an internal holding area for holding liquid cryogen;
   at least one cryoprobe outside said container for use in cryotherapeutic procedures;
   a heat exchanger disposed within the container, the heat exchanger comprising:
      a substantially cylindrical inner chamber having an outer wall and an internal lumen with a central longitudinal axis, the inner chamber providing a flow path for the liquid cryogen to the at least one cryoprobe, the internal lumen including a plurality of baffles extending from the outer wall into the flow path of the liquid cryogen flowing through the inner chamber and an interior central component, wherein
         i) the interior central component is centrally positioned within the inner lumen along the central longitudinal axis;
         ii) the flow path of the liquid cryogen flowing through the inner chamber is provided between the centrally positioned interior central component and the outer wall, and
         iii) the interior central component is configured to circulate the flow of liquid cryogen flowing through the inner chamber in a corkscrew path around an exterior of the centrally positioned interior central component thereby increasing the flow path of the liquid cryogen flowing through the inner chamber; and
      an outer chamber defined between the outer wall of the inner chamber and an outer wall of the heat exchanger configured to be filled with the liquid cryogen, wherein a vacuum can be drawn on the outer chamber to reduce a pressure and temperature of the liquid cryogen within the outer chamber;
   a pump which delivers the liquid cryogen to said heat exchanger to subcool the liquid cryogen;
   an exit port configured to attach said at least one cryoprobe;
   at least one supply line connected to said heat exchanger and to said exit port, said at least one supply line directing the liquid cryogen to said at least one cryoprobe; and
   at least one return line which returns liquid cryogen to the container;
   wherein said container integrates said at least one supply line and said at least one return line with said heat exchanger to form a closed system.

2. The cryogenic system of claim 1, wherein said closed system is electronically controlled or computer operated.

3. The cryogenic system of claim 1, wherein said container is a vacuum insulated dewar.

4. The cryogenic system of claim 1, wherein said outer chamber is a subcooling chamber that surrounds said inner chamber and wherein said outer chamber is connected to a vacuum source.

5. The cryogenic system of claim 4, wherein said vacuum source connects to said at least one cryoprobe.

6. The cryogenic system of claim 1, wherein said heat exchanger subcools the liquid cryogen to a reduced temperature prior to delivery to said cryoprobe.

7. The cryogenic system of claim 1, further comprising a return chamber within said container and surrounding said at least one supply line between an exit opening of said heat exchanger and said exit port, said return chamber comprising one or more vents configured to vent contents of the return chamber into the container, said return chamber configured for receiving the liquid cryogen returned from said at least one cryoprobe by way of said at least one return line, said one or more vents allowing for reutilization of the liquid cryogen.

8. The cryogenic system of claim 7, wherein said return chamber includes a secondary heat exchanger, said at least one return line passing through said secondary heat exchanger to subcool the liquid cryogen in said at least one return line.

9. The cryogenic system of claim 7, further comprising a plurality of controlled valves, heaters, sensors, motors, or gauges for maintaining consistent operations of temperature and pressure variations within said closed system.

10. The cryogenic system of claim 1, wherein said container which receives the liquid cryogen returned from said at least one cryoprobe insulates said at least one supply line and said at least one return line.

11. The cryogenic system of claim 1 wherein:
   the outer chamber of the heat exchanger is a subcooling chamber;
   the pump is a submersible pump that delivers liquid cryogen in said container to said outer chamber of said heat exchanger to subcool the cryogen is connected to said heat exchanger by a valve;

said at least one return line is connected to said at least one cryoprobe and configured to return liquid cryogen from said at least one cryoprobe to the container; and said container fluidly connecting said at least one supply line and said at least one return line with said submersible pump, said valve connecting said submersible pump to said heat exchanger to form said closed system.

12. The cryogenic system of claim 11, wherein said cryogenic system is not a compression based bellows system.

13. The cryogenic system of claim 11, comprising:

said at least one supply line connecting said pump to said heat exchanger and exiting said heat exchanger to said exit port, wherein said at least one supply line connecting said heat exchanger to said exit port delivers the liquid cryogen to said at least one cryoprobe;

a return chamber in said internal area of said container and surrounding said one or more supply lines; and said at least one return line connecting said return chamber to said at least one cryoprobe through said exit port, said return chamber configured for receiving liquid cryogen returned from said at least one cryoprobe by way of said at least one return line, wherein said return chamber comprises one or more vents configured to vent contents of said return chamber into said internal lumen of said container allowing for reutilization of the liquid cryogen;

wherein, said one or more walls of said container include (i) one or more openings that allow for venting of excess gas or liquid overflow, and (ii) at least one opening providing an exit port where said at least one cryoprobe is attached, said internal area of said container comprising liquid cryogen; said pump being positioned within said container, said pump delivering the liquid cryogen to said heat exchanger to subcool the cryogen;

said heat exchanger being positioned within said internal area of said container, and said at least one supply line and said at least one return line form a closed system that provides for supply and return of the liquid cryogen to said heat exchanger within said internal area of said container, said heat exchanger providing an enhanced surface area for reducing temperature of the liquid cryogen.

14. A method of delivering liquid cryogen to at least one cryoprobe, said method comprising the steps of:

providing the cryogenic system claim 11, filling said cryogenic system with the liquid cryogen;

pumping the liquid cryogen through said pump and into said heat exchanger;

subcooling the liquid cryogen within said heat exchanger;

delivering the liquid cryogen through said at least one supply line to said exit port which attaches to said at least one cryoprobe;

returning the liquid cryogen through said at least one return line into a return chamber of said device; and recirculating the liquid cryogen through said cryogenic system for reuse in delivering liquid cryogen to said at least one cryoprobe.

15. The method of claim 14, wherein: the internal lumen of said heat exchanger connects to the at least one supply line from the pump and to the exit port, and is configured for liquid cryogen to flow through the internal lumen of the inner chamber comprising a plurality of baffles extending into the flow path of the liquid cryogen and providing an enhanced surface area for reducing the temperature of the liquid cryogen within said heat exchanger.

16. The method of claim 14, further comprising a step of pressurizing the liquid cryogen within said closed system such that one or more control valves positioned therein are capable of being electronically manipulated.

17. The method of claim 14, wherein the step of subcooling the liquid cryogen within said heat exchanger includes a step of increasing the flow path, of the liquid cryogen within said heat exchanger.

18. The method of claim 17, wherein said internal lumen of said heat exchanger inner chamber includes a plurality of baffles and an internal component that circulates the liquid cryogen in the inner chamber.

19. The cryogenic system of claim 1, wherein said cryogenic system is not a compression based bellows system.

20. The cryogenic system of claim 1, wherein said plurality of baffles is a plurality of discontinuous baffles.

21. A cryogenic system comprising:

a container comprising liquid cryogen;

at least one cryoprobe outside said container for use in cryotherapeutic procedures;

a heat exchanger disposed within the container and surrounded by a subcooling chamber, wherein the heat exchanger and subcooling chamber are disposed within the container and said heat exchanger comprising a substantially cylindrical inner chamber having an outer wall and an internal lumen with a central longitudinal axis, the inner chamber providing a flow path for the liquid cryogen to the at least one cryoprobe, the internal lumen including a plurality of baffles extending from the outer, wall into the flow path of the liquid cryogen flowing through the inner chamber and an interior central component, wherein i) the interior central component is centrally positioned within the inner lumen along the central longitudinal axis;

ii) the flow path of the liquid cryogen flowing through the inner chamber is provided between the centrally positioned interior central component and the outer wall, iii) the interior central component is configured to circulate the flow of liquid cryogen flowing through the inner chamber in a corkscrew path around an exterior of the centrally positioned interior central component thereby increasing the flow path of the liquid cryogen flowing through the inner chamber; and iv) the subcooling chamber defined between the outer wall of the substantially cylindrical inner chamber and an outer wall of the heat exchanger and being filled with the liquid cryogen, wherein a vacuum is drawn on the subcooling chamber to reduce a pressure and temperature of the liquid cryogen within the subcooling chamber; and a pump which delivers the liquid cryogen to said heat exchanger to subcool the cryogen;

an exit port configured to attach said at least one cryoprobe;

at least one supply line connected to said heat exchanger and to said exit port, said a least one supply line directing the liquid cryogen to said at least one cryoprobe; and at least one return line which returns liquid cryogen to the container;

wherein said container integrates said at least one supply line and said at least one return line with said heat exchanger to form a closed system, said cryogenic system further comprising a return chamber surrounding said at least one supply line between an exit opening of said heat exchanger and said exit port, said return chamber receiving the liquid cryogen returned from said at least one cryoprobe by way of said at least one return line, and a series of controlled valves, heaters, sensors, motors, or gauges for maintaining consistent operations of temperature and pressure variations within said closed system.

22. The cryogenic system of claim 21, wherein said cryogenic system is riot a compression based bellows system.

23. The cryogenic system of claim 21, wherein said plurality of baffles is a plurality of discontinuous baffles.

\* \* \* \* \*